United States Patent
Carmel et al.

(10) Patent No.: US 7,166,103 B2
(45) Date of Patent: Jan. 23, 2007

(54) HIGH EFFICIENCY ELECTROSURGICAL ABLATOR WITH ELECTRODE SUBJECTED TO OSCILLATORY OR OTHER REPETITIVE MOTION

(75) Inventors: Yuval Carmel, Rockville, MD (US); Anatoly Shkvarunets, Rockville, MD (US); Robert A. Van Wyk, Largo, FL (US)

(73) Assignee: Electrosurgery Associates, LLC, Rockville, MD (US)

( * ) Notice: Subject to any disclaimer, the term of this patent is extended or adjusted under 35 U.S.C. 154(b) by 0 days.

(21) Appl. No.: 10/211,258

(22) Filed: Aug. 5, 2002

(65) Prior Publication Data
US 2003/0065321 A1 Apr. 3, 2003

Related U.S. Application Data

(60) Provisional application No. 60/326,147, filed on Sep. 25, 2001.

(51) Int. Cl.
*A61B 18/18* (2006.01)

(52) U.S. Cl. ............... 606/41; 606/42; 606/45; 606/49; 606/171; 606/180; 128/898; 607/104; 607/105; 604/22

(58) Field of Classification Search ............. 606/41, 606/42, 45–50, 170, 171, 180; 607/101, 607/104, 105; 604/22; 128/898
See application file for complete search history.

(56) References Cited

U.S. PATENT DOCUMENTS

| | | | |
|---|---|---|---|
| 5,190,517 A | * | 3/1993 | Zieve et al. .............. 604/22 |
| 5,282,799 A | * | 2/1994 | Rydell .................... 606/48 |
| 5,527,331 A | * | 6/1996 | Kresch et al. ............ 606/170 |
| 5,554,112 A | | 9/1996 | Walbrink et al. |
| 5,830,214 A | * | 11/1998 | Flom et al. .............. 606/41 |
| 5,873,855 A | * | 2/1999 | Eggers et al. ............ 604/114 |
| 6,015,406 A | | 1/2000 | Goble et al. |
| 6,050,993 A | * | 4/2000 | Tu et al. ................. 606/41 |
| 6,159,209 A | * | 12/2000 | Hakky .................... 606/45 |
| 6,165,206 A | | 12/2000 | Tu |
| 6,214,003 B1 | * | 4/2001 | Morgan et al. ........... 606/50 |
| 6,558,382 B1 | * | 5/2003 | Jahns et al. .............. 606/41 |
| 6,565,561 B1 | * | 5/2003 | Goble et al. ............. 606/41 |
| 6,702,831 B1 | * | 3/2004 | Lee et al. ................ 606/159 |

FOREIGN PATENT DOCUMENTS

GB 2327352 A 1/1999

* cited by examiner

*Primary Examiner*—Rosiland Rollins
(74) *Attorney, Agent, or Firm*—Dickstein Shapiro LLP

(57) ABSTRACT

A high efficiency electrosurgical ablator which is subjected to a combined oscillatory and mechanical debridement motion during resection of tissue is disclosed. The electrosurgical ablator is positioned in the proximity of the tissue to be treated in the presence of an electrically conductive fluid. A high frequency voltage is applied to the electrode of the ablator, and the electrode is subjected to an oscillatory or other repetitive motion created by an element located within the ablator assembly. The ablator electrode is further connected to a suction assembly that supplies suction from an external source.

7 Claims, 5 Drawing Sheets

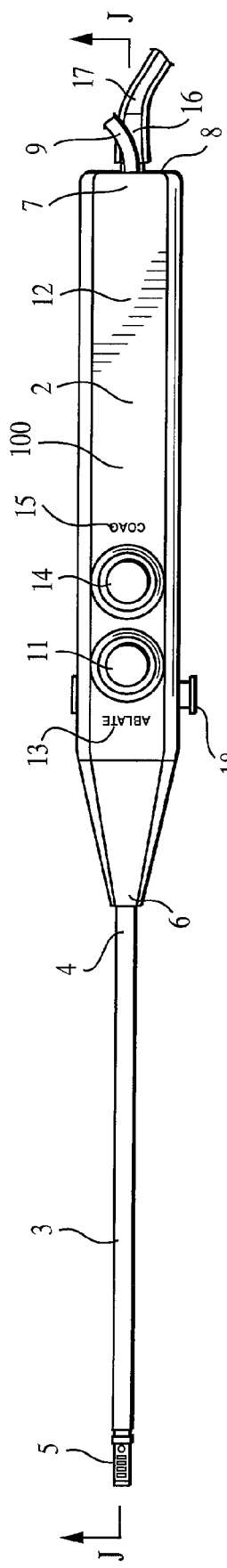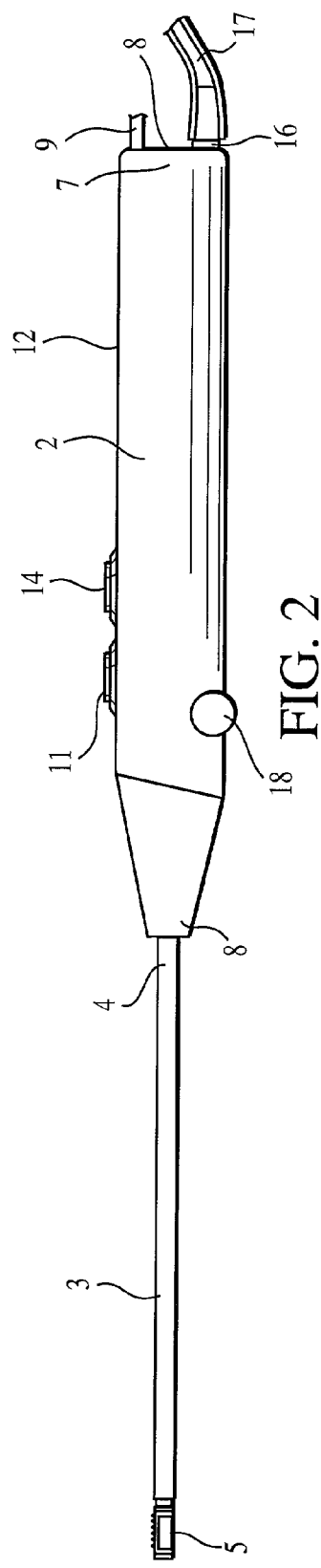

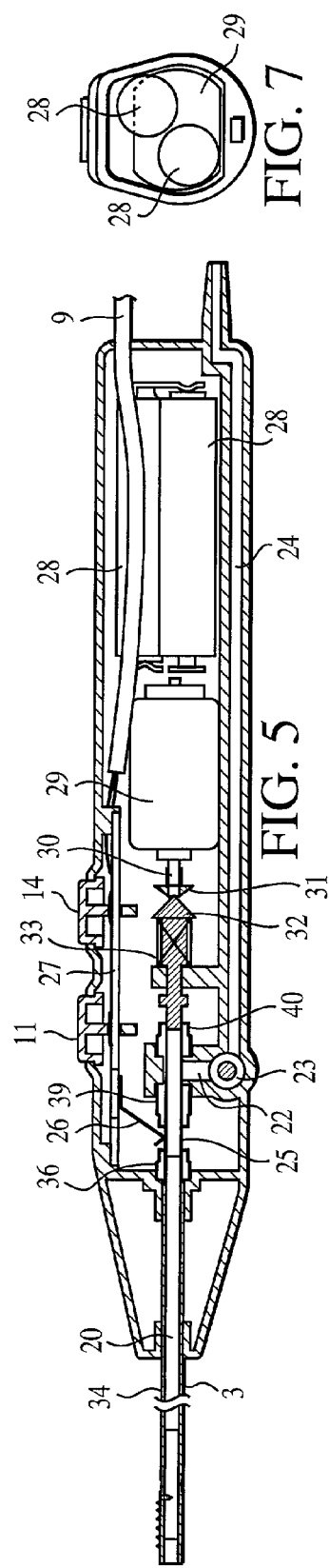
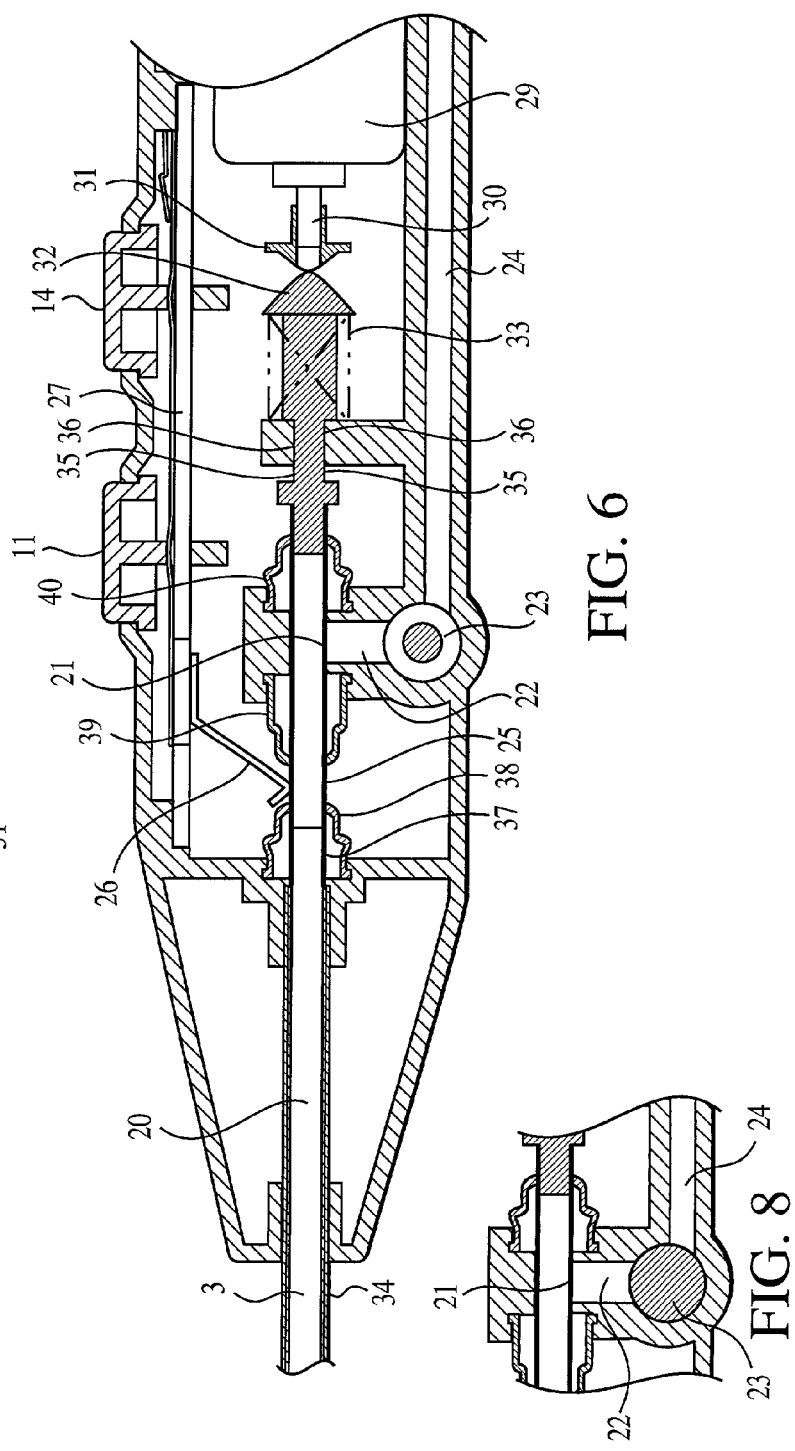

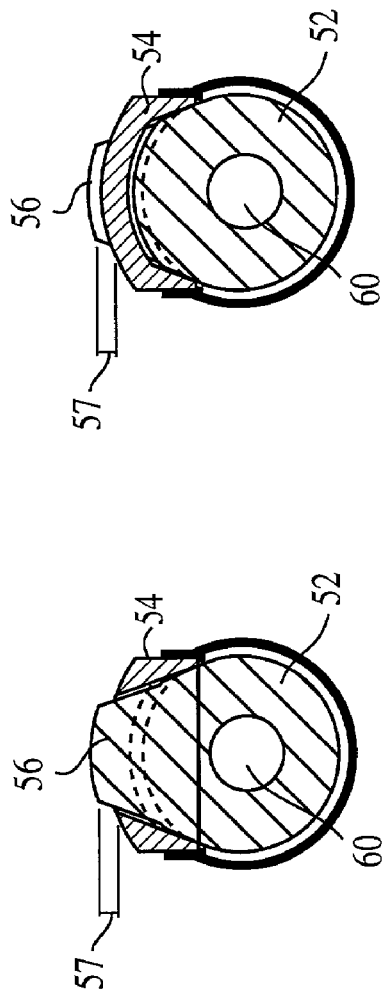
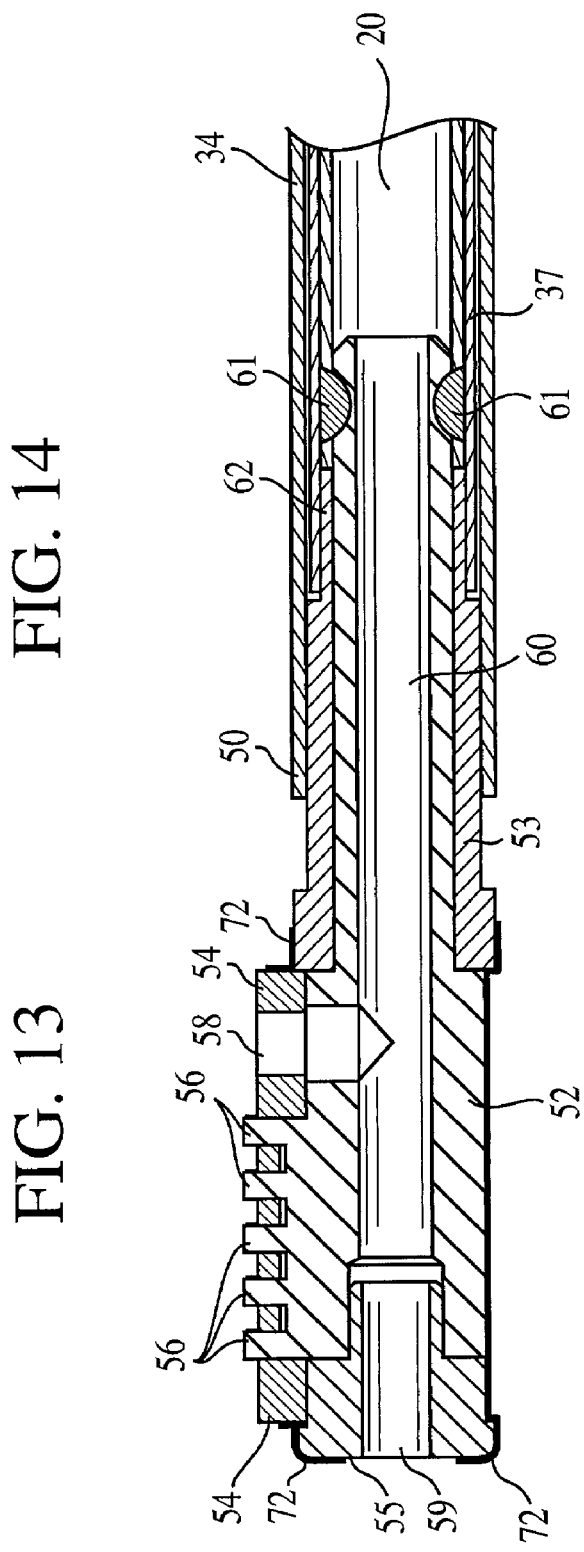

HIGH EFFICIENCY ELECTROSURGICAL ABLATOR WITH ELECTRODE SUBJECTED TO OSCILLATORY OR OTHER REPETITIVE MOTION

The present application claims the benefit under 35 U.S.C. 119(e) of U.S. Provisional Application Ser. No. 60/326,147 filed on Sep. 25, 2001, the disclosure of which is incorporated by reference herein.

FIELD OF THE INVENTION

The present invention relates to the field of electrosurgery and, in particular, to electrosurgical devices and methods which employ high frequency voltage to cut, ablate or coagulate tissue in a fluid environment.

BACKGROUND OF THE INVENTION

Electrosurgical procedures typically rely on the application of high frequency or radio frequency (RF) electrical power to cut, ablate or coagulate tissue structures. For example, electrosurgery cutting entails heating tissue cells so rapidly that they explode into steam leaving a cavity in the cell matrix. When the electrode is moved and fresh tissue is contacted, new cells explode and the incisions is made. Such electrosurgical cutting involves the sparking of the current to the tissue, also known as the jumping of the RF current across an air gap to the tissue.

Radiofrequency electrodes employed in electrosurgical procedures are generally divided into two categories: monopolar devices and bipolar devices. In monopolar electrosurgical devices, the RF current generally flows from an exposed active electrode through the patient's body, to a passive or return current electrode that is externally attached to a suitable location on the patient's skin. In bipolar electrosurgical device, both the active and the return current electrodes are exposed and are typically in close proximity. The RF current flows from the active electrode to the return electrode through the tissue. Thus, in contrast with the monopolar electrosurgical devices, the return current path for a bipolar device does not pass through the patient's body.

Electrosurgery which takes place in a conductive fluid environment, such as inside of a joint or body cavity filled with, for instance, normalized saline solution, differs from that described previously in that current is conducted from the active electrode through the fluid to the return electrode. In the case of a monopolar device, the current flows through the patient to the return electrode in the manner previously described. In the case of bipolar devices operating in a conductive fluid environment, the return electrode is not in contact with tissue, but rather is submerged in the conductive fluid in proximity with the active electrode. Current flow is from the active electrode through the conductive liquid and surrounding tissues to the return electrode of the bipolar device. Whether an electrode is monopolar or bipolar, current flows from all uninsulated surfaces of the active electrode to the return electrode whenever the electrode is energized. This is in contrast to conventional surgery (also called "open surgery") in which current flows only through electrode surfaces in contact with the patient's tissue.

For an electrode in a fluid environment to vaporize tissue, as in the cutting process described previously, the current density at the electrode/tissue interface must be sufficiently high to cause arcing between the electrode and the patient. If such current density is not achieved, power flows from the active electrode to the return electrode with no desirable clinical effect. In fact, such current flow is highly undesirable since the current flowing from the active electrode heats the conductive fluid and a tissue in the region surrounding the active electrode. A surgeon using a device which is energized but not arcing to the tissue may believe that he is not affecting tissue in close proximity to the active electrode, however, he may be subjecting the tissue to temperatures approaching 100° C. Even when the electrode is arcing to the tissue, the thermal effects are not limited to vaporization of the tissue. Appreciable undesirable heating of the fluid and tissue in the vicinity to the electrode takes place.

One way of avoiding the negative effects of the undesirable heating of the fluid and adjacent tissue structures is to set the power of the electrosurgical generator to a level that is low enough to minimize the heating of the liquid but high enough to produce sparks. There is an inherent difficulty, however, in satisfying acceptable electrosurgical parameters, since virtually all electrosurgical electrodes are "ignited," i.e., generate sparks, only when brought into contact with tissue, and then, generally, after a time delay of varying lengths. At the instant when sparks are not generated, most of the RF power supplied to an electrode operating in a conducting fluid is dissipated in the fluid itself as heat, consequently raising the temperature of the fluid within the joint and the adjacent tissue. At the instant when sparks are generated, the RF power is used for the creation of sparks in the vicinity of the electrodes. Therefore, energizing the electrosurgical electrode without initiation of sparks is dangerous and undesirable, as the heating may damage tissue structure uncontrollably in surrounding areas and also deep under the surface.

During the past several years, specialized arthroscopic electrosurgical electrodes also called ablators have been developed for arthroscopic surgery. Ablator electrodes differ from conventional arthroscopic electrosurgical electrodes in that they are designed for the bulk removal of tissue by vaporization, rather than by cutting the tissue or coagulating the bleeding vessels. This way, during ablation, volumes of tissue are vaporized rather then discretely cut out and removed from the surgical site.

The power requirements of ablator electrodes are generally higher than those of other arthroscopic electrodes. The efficiency of the electrode design and the characteristics of the radio frequency (RF) power supplied to the electrode also affect the amount of power required for ablation. For example, electrodes with inefficient designs and/or powered by RF energy with poorly suited characteristics will require higher power levels than those with efficient designs and appropriate generators. As a result, the ablation power levels of devices produced by different manufactures vary widely, with some manufactures using power levels significantly higher than those commonly used by arthroscopic surgeons. For example, ablator electrode systems from some manufacturers may use up to 280 Watts, significantly higher than the 30 to 70 Watt range generally used by other arthroscopic electrosurgical electrodes.

The amount of fluid temperature increase within a joint and, consequently, the temperature of the adjacent tissue is critical during the use of ablator electrodes. The fluid temperature may easily reach 45° C., at which cell death typically occurs, and this temperature is easily reached with high-powered ablators operating when sufficient flow is not used. The increase in the fluid temperature is also directly proportional to the increase in the power level. As such, the fluid temperature increases as the period of time necessary for an electrosurgical ablator to be energized increases. Standard arthroscopic electrosurgical electrodes are generally energized for only brief periods (generally measured in seconds) while specific tissue is resected or modified. In contrast, ablator electrodes are energized for longer periods of time (often measured in minutes) while volumes of tissue are vaporized.

During ablation, current flow from the ablator into the conductive fluid heats the fluid to its boiling point. Initially, steam bubbles form only at the edges of the ablator, but eventually they cover the entire surface of the electrode. The electrical resistance to current flow increases to its maximum value, maximum voltage is applied to the steam gap, and sparking occurs within the bubble. Sparking within the bubble destroys the tissue which is within the same bubble. After the tissue is destroyed, the sparking continues but no beneficial destruction takes place until new tissue is brought into contact with the active region of the probe. In practice, this is done by manual mechanical movement of the probe, which is conducted manually by the surgeon. Typically, the surgeon uses a sweeping or oscillating back-and-forth motion during tissue removal. Indeed, a surgical technique has a large effect on the efficiency with which an ablator operates.

During the time when sparking does not occur, that is, when the emerging bubbles have not yet reached critical size or when sparking occurs without tissue in the active zone of the electrode, power is flowing from the electrode into the operating region without tissue being ablated. Furthermore, current flow into the fluid during this time causes heating of the fluid with no desirable clinical effect to the patient. Because no tissue is removed during this unproductively sparking or "non-sparking" period, an ablator operating with large unproductive time is inefficient. To achieve an acceptable rate of tissue ablation would require increasing the power supplied to the ablator. As discussed previously, however, increasing the power level increases the rate of heating of the fluid in the joint which, in turn, increases the likelihood of thermal injury to the patient.

In many instances, ablators are used to clean tissue from bony surfaces. The surgeon moves the ablator over the surface with a sweeping or scrubbing motion. This motion causes the ablator to brush over and against the surface of the bone leading to enhanced tissue removal, because it produces a combination of electrosurgical/ablative action and mechanical debridement and also because it causes accelerated removal of spent bubbles.

The scrubbing motion and combination of mechanical debridement and electrosurgical action are particularly important when ablating articular cartilage. Generally, tissue is removed from bone to clear the surface of the bone so that it can be subsequently shaped or sculpted with a bur, thereby removing the ablated surface. Since this bone is subsequently removed, exposure to localized, transient, high temperatures is generally of no concern. In contrast, the surface and subsurface cartilage remaining after the smoothing of lesions is not removed and it is necessary that thermal damage be minimized. The mechanical properties of articular cartilage cause it to respond well to a combination of mechanical debridement and electrosurgical action. This type of action also enhances electrode efficiency through "tissue-bubble management," thereby reducing power requirements and local fluid temperatures. Unfortunately, this method is technically demanding and results will vary widely according to the surgical technique employed, as the electrode motions must be closely controlled.

Accordingly, there is a need to minimize the unproductive "non-sparking" or idle-sparking time of an electrosurgical ablator electrode to achieve improved tissue removal rates at low power levels. There is also a need for an electrosurgical ablator electrode of high efficiency using "tissue-bubble management" at the ablator tip to minimize the dead time between trains of pulses by employing an oscillatory motion. An ablator of high efficiency capable of producing a combination of electrosurgical ablation and mechanical debridement through an oscillatory or other repetitive motion is also needed.

BRIEF SUMMARY OF THE INVENTION

In one aspect, the invention provides a high efficiency electrosurgical ablator capable of producing a fast and slight repetitive motion along with mechanical debridement by the ablator electrode concurrent with ablation. The electrosurgical ablator is linked to an element capable of imparting an oscillatory or other repetitive motion to the ablator electrode which is located within the instrument itself. The electrosurgical ablator is also linked to a suction assembly that supplies suction from an external source to a handle of the electrosurgical ablator. The suction assembly comprises means for transmitting suction to an inner lumen of the ablator electrode and a suction control region for regulating the level of suction transmitted.

In another aspect, the invention provides an apparatus for conducting electrosurgical procedures or interventions comprising at least one electrosurgical probe that includes an element capable of imparting an oscillatory or other repetitive motion, which is located within the electrosurgical probe itself, and which is in contact with a suction assembly.

The invention also provides a method of employing an electrosurgical ablator in an electrosurgical procedure during which ablation and mechanical debridement are simultaneous when the ablator electrode is in contact with the tissue structure. The method comprises the steps of: (i) positioning an ablator electrode adjacent a target tissue; (ii) connecting the ablator electrode to an external vacuum source; then (iii) either submerging the target tissue in an electrical conducting fluid or (iv) directing an electrically conducting fluid to the target tissue; and (v) subjecting the ablator electrode to an oscillatory or other repetitive motion to bring the active zone of the electrode to a region of fresh, yet undestroyed, tissue.

These and other features and advantages of the invention will be more apparent from the following detailed description that is provided in connection with the accompanying drawings and illustrated exemplary embodiments of the invention.

BRIEF DESCRIPTION OF THE DRAWINGS

FIG. 1 is a plan view of an electrosurgical probe according to an embodiment of the present invention.

FIG. 2 is a side view of the electrosurgical probe of FIG. 1.

FIG. 3 is a distal end view of the electrosurgical probe of FIG. 2.

FIG. 4 is a proximal end view of the electrosurgical probe of FIG. 2.

FIG. 5 is a cross-sectional view taken along line J—J.

FIG. 6 is an enlarged partial proximal end view of the electrosurgical probe of FIG. 2.

FIG. 7 is an enlarged view of the distal portion of the electrosurgical probe of FIG. 5.

FIG. 8 is a schematic view of the suction control region of FIG. 7.

FIG. 13 is a lateral cross-sectional view of the electrosurgical probe of FIG. 10 taken along line A—A.

FIG. 14 is a lateral cross-sectional view of the electrosurgical probe of FIG. 11 taken along line B—B.

FIG. 15 is a side cross-sectional view of the electrosurgical probe of FIG. 11 taken along line C—C.

DETAILED DESCRIPTION OF THE PREFERRED EMBODIMENTS

Figure 12:
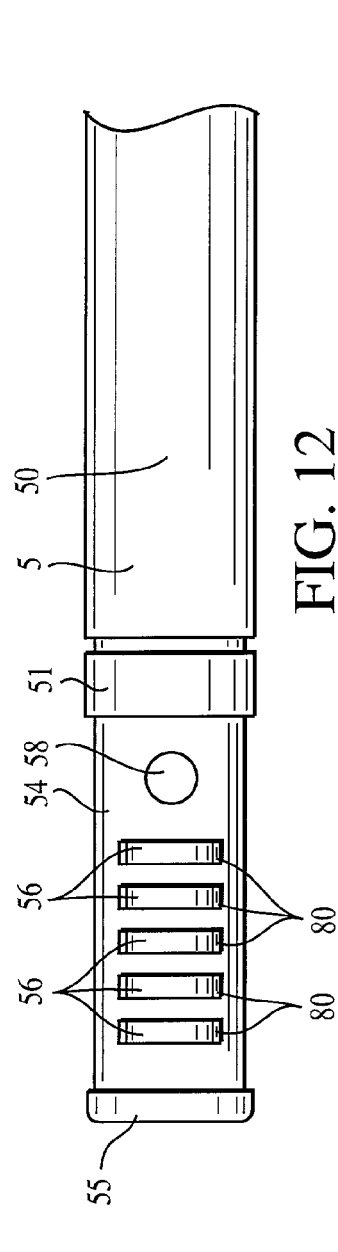
FIG. 12 is a view of the distal tip of the electrosurgical probe of FIG. 10.

The present invention provides a high efficiency electrosurgical ablator electrode capable of producing a fast and slight oscillatory motion during ablation while allowing mechanical debridement concurrent with ablation. The electrosurgical ablator electrode is linked to an element capable of imparting an oscillatory or other repetitive motion to the ablator electrode and located within the ablator electrode. The electrosurgical ablator electrode is further connected to a suction assembly that supplies suction from an external vacuum source to the ablator.

As described in detail below, the oscillatory motion may be imparted by an electric motor mounted coaxial with a tubular distal section of the ablator electrode comprising a fixed outer tube and an inner tube free to move axially within the fixed outer tube. The electric motor is in contact with a cam/follower mechanism that imparts the oscillatory motion on the inner tube. Rotation of the electric motor produces oscillations of the inner tube, the amplitude of the oscillations being determined according to the design of the cam affixed to the electric motor. The repetitive motion may be further imparted by an electromechanical motor, a piezoelectric device, an electromagnet, a rotating device, or electric energy extracted from an RF generator, among others.

As described in more detail below, the present invention contemplates the use of a single active electrosurgical electrode, or of an array of such active electrosurgical electrodes distributed over a distal surface of an electrosurgical probe, the electrosurgical electrode or electrodes being subjected to an oscillatory motion.

Referring now to the drawings, where like elements are designated by like reference numerals, FIGS. 1–15 illustrate an exemplary embodiment of an electrosurgical ablator electrode 100 fabricated according to the present invention. The electrosurgical ablator electrode 100 of FIGS. 1–15 may be used, for example, in the treatment of body tissue in minimally invasive procedures within the body, for example, in procedures that require the introduction of a surgical instrument through a percutaneous penetration or through a natural opening in the patient. Although, for simplicity, the invention will be described below with reference to a monopolar electrode, such as the electrosurgical ablator electrode 100, the invention has equal applicability to systems employing bipolar electrosurgical electrodes.

As illustrated in FIGS. 1–4, the electrosurgical ablator electrode 100 has a proximal region which comprises a handle 2 and an elongated distal portion 3. The elongated distal portion 3 comprises a proximal end 4 and a distal end 5 having a configuration suitable for arthroscopic ablation of tissue. The proximal end 4 of the elongated distal portion 3 is rigidly affixed to distal end 6 of the handle 2.

The elongated distal active portion 3 (FIG. 1) of the electrosurgical ablator electrode 100 having a combined oscillatory and mechanical debridement motion comprises a metallic body region and preferably a metallic tip located at the distal end of the metallic region. The metallic body region and the metallic tip located at the distal end of the metallic region may have various cross-sectional shapes and geometries, for example, cylindrical, rectangular, or elipsoidal, among many others. The metallic body region and the metallic tip may be formed of electrically conductive materials such as metals and metal alloys, for example, stainless steel and stainless steel alloys, platinum and platinum alloys, gold and gold alloys, nickel and nickel alloys, titanium and titanium alloys, and molybdenum and molybdenum alloys, among others.

If desired, the metallic body region may be covered with and insulated by a dielectric material, which may comprise an electrically insulating material such as epoxy, plastic, silicon-based material, ceramic, glass or compositions of these mentioned materials, among many others. The dielectric material may also comprise a perforated shield also formed of an electrically insulating material which may be porous and which may include an opening that allows an electrically conductive liquid, for example an isotonic saline solution, to contact the metallic tip and the target tissue.

If a dielectric material is employed, sufficient clearance must exist between the inner surface of the dielectric material and the outer surface of metallic body region to allow thermal expansion of the metallic body without cracking the dielectric material, particularly at the distal end of the items. The metallic body region may be bonded to the dielectric material by a sealing material which is typically an inorganic sealing that provides effective electrical insulation and good adhesion to both the dielectric material and the metallic body region. The sealing material may preferably have a compatible thermal expansion coefficient and a melting point above the temperature reached in the region during use.

Although, for simplicity, the embodiments of the present invention will be described below with reference to only one elongated distal active portion 3 having an oscillatory motion as part of the electrosurgical ablator electrode 100, the invention is not limited to this exemplary embodiment. Accordingly, the invention also contemplates the formation of a plurality of such elongated distal active portions as part of an electrosurgical electrode.

Proximal end 7 (FIGS. 1–4) of the handle 2 has a proximal-most face 8 through which an electrical cord 9 passes to connect the probe to a standard electrosurgical power supply or generator (not shown). The power supply provides very high frequency or radio frequency (RF) voltage to the electrosurgical ablator electrode 100. The power supply may be also provided with an operator-controllable voltage level adjustment to control the applied voltage level. Thus, a surgeon or a medical operator may manually adjust the voltage level applied to electrosurgical ablator electrode 100 through a voltage level adjustment.

As further illustrated in FIGS. 1–4, a first button 11 protrudes from an upper surface 12 of the handle 2 and near distal end 6 of the handle 2. The first button 11 has a label 13 marked "ABLATE." Depressing the first button 11 activates the electrosurgical generator and causes RF energy suitable for arthroscopic ablation of tissue to be supplied to the electrosurgical ablator electrode 100. A second button 14 protrudes from the upper surface 12 of the handle 2 and slightly proximal to the first button 11. The second button 14 has a label 15 marked "COAG." Depressing the second button 14 activates the electrosurgical generator and causes RF energy suitable for arthroscopic coagulation of bleeding vessels to be supplied to the electrosurgical ablator electrode 100. Thus, in the "ablation" mode, a sufficient voltage is applied to the electrosurgical ablator electrode 100 to ablate the target tissue. The requisite voltage level depends on the number, size and spacing of the electrodes. Similarly, in the "coagulation" mode, a sufficiently low voltage is applied to the electrosurgical ablator electrode 100 so to avoid vaporization of the electrically conductive fluid.

As also illustrated in FIGS. 1–4, a tapered tubular section 16 protrudes from the proximal-most face 8 of the handle 2 and connects to a flexible tube 17. The flexible tube 17 is further connected to a vacuum source (not shown) at its proximal end. A slide-type control 18 is located near the distal end 6 of the handle 2 and towards the bottom of the handle 2, as illustrated in FIGS. 1–4. Positioning the control slide 18 to the right, for example, causes suction supplied by the flexible tube 17 to be further supplied to the distal portion 3. Conversely, positioning the control slide 18 to the left prevents the supply of suction supplied by the flexible tube 17 to the distal portion 3.

As illustrated in FIGS. 5–8, suction from the tapered tubular section 16 is supplied to an inner lumen 20 of the elongated distal section 3 via orifice 21, passage 22, slide control 23 and passage 24. Surfaces of the inner lumen 20 are coated with a polymeric material 65. As shown in more detail in FIG. 8, positioning the slide control 23 to the closed position blocks the flow from the passage 22 to the passage 24. If desired, the slide control 23 could only partially block the flow from the passage 22 to the passage 24.

FIGS. 5 and 6 depict in detail the path for the transmission of RF energy from the electrical cord 9 to the tip of the distal end 5 of the distal portion 3 of the electrosurgical ablator electrode 100. The RF energy produced by the electrosurgical generator is transmitted from the electrical cord 9 to a distal portion of the inner tube 25 via spring 26 and switch 27. The switch 27 is positioned beneath the first and second buttons 11, 14 so that depressing either the first button 11 or the second button 14 causes closure of the required electrical connection to produce a desired action by the electrosurgical generator.

The switch 27 is provided with an additional set of electrical contacts activated by depressing the first button 11 which, in turn, causes power to be supplied from batteries 28 to electric motor 29 simultaneously with the supply of RF energy to the inner tube 25. Output shaft 30 of the electric motor 29 is fitted with a cam 31 that rotates when the first button 11 is depressed. The cam 31 is designed to produce axial motion when rotated through the profile formed by its distal surface. Coaxial with the output shaft 30 and the cam 31 is a follower 32, which is mounted to the inner tube 25 and held in contact with the cam 31 by compression spring 33. The inner tube 25 is free to move axially within outer tube 34. The follower 32 is a metallic piece designed to "follow" or stay in contact with the distal face contour of the cam 31 to produce an oscillatory motion in the follower 32 and the movable inner tube 25 to which it is affixed.

Angular alignment of the follower 32 and of the inner tube 25 is maintained by laterally opposed and parallel planar faces 35, which are in sliding contact with a mating slot 36 in the handle 2. Contact between the follower 32 and the cam 31 is maintained by a compression spring mounted coaxially with the follower 32 and placed between the follower 32 and the interior of the handle 2 so as to produce a proximal force on the follower 32.

Energizing the electric motor 29 causes an oscillatory motion in the inner tube 25 and within the stationary outer tube 34. The inner tube 25 is electrically isolated from the outer tube 34 by an insulating tubing 37, for example, a polymeric insulating tubing 37. Seal 38 prevents flow of fluid in the gap between the polymeric insulating tubing 37 and the outer tube 34 from entering the interior of the handle 2. Seals 39 and 40 also prevent vacuum in the passage 22 from leaking into the interior of the handle 2. Seals 38, 39 and 40 are flexible so that seal integrity is maintained during oscillation of the inner tube 25.

Figure 9:
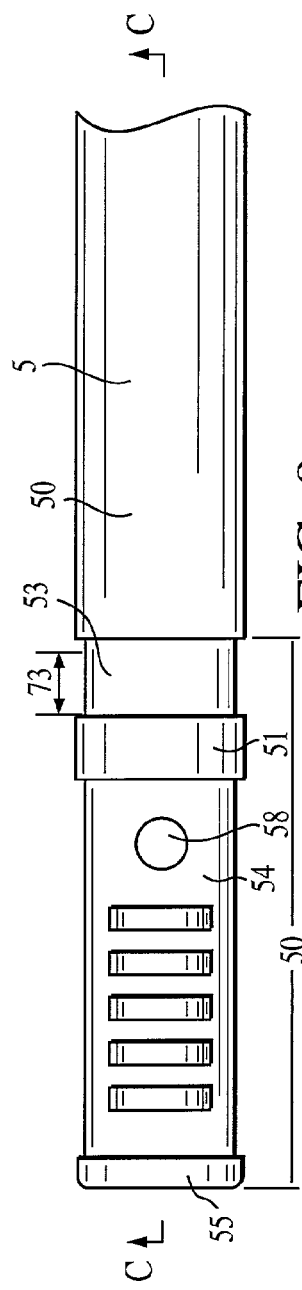
FIG. 9 is a plan view of the distal tip of the electrosurgical probe of FIG. 1 with the electrode in the retracted position.
Figure 10:
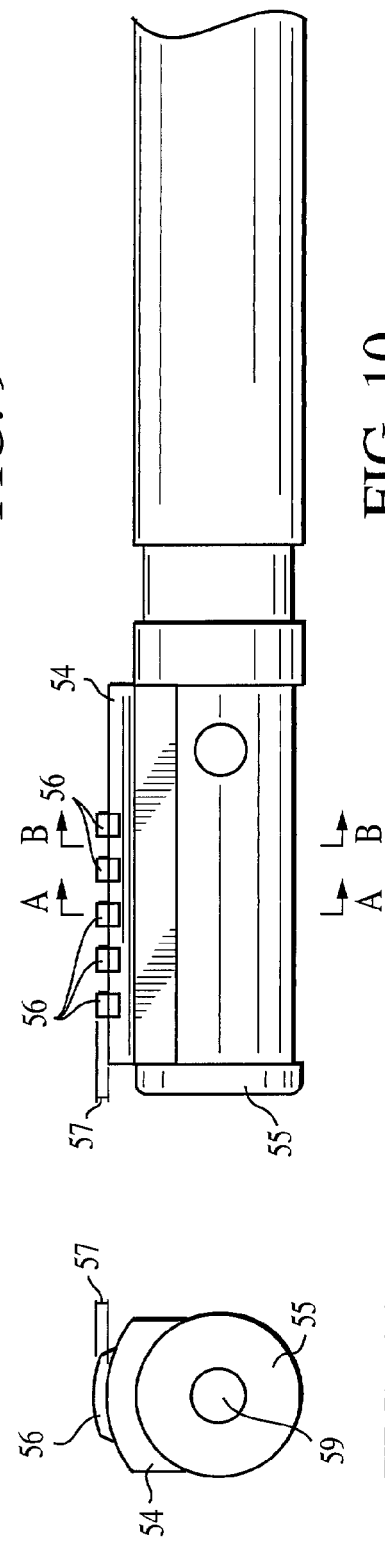
FIG. 10 is a plan view of the distal tip of the electrosurgical probe of FIG. 1 with the electrode in the extended position.
Figure 11:
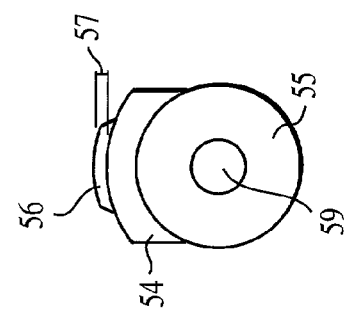
FIG. 11 is a side view of the electrosurgical probe of FIG. 10.

Referring now to FIGS. 9–15, the distal end 5 of the elongated distal portion 3 comprises a fixed portion 50, which is the far distal tip of the outer tube 34, and a movable portion 51, which is attached to the distal end of the inner tube 25. The movable portion 51 is an assembly comprising a mandrel 52, a cylindrical dielectric insulator 53, a ceramic top insulator 54 and an insulator tip 55 made from ceramic or polymeric material. The inner surface of mandrel 52 and inner tube 25 are covered with an insulator coating 65 to prevent current flow from the mandrel and the inner tube to saline in the inner lumen. As illustrated in FIGS. 9–15, the mandrel 52 has ribs 56 protruding from its upper surface through corresponding slots 80 in the ceramic top insulator 54. The ribs 56 protrude from the ceramic top insulator 54 by a distance 57 (FIGS. 10–11).

Annular opening 58 in the ceramic top insulator 54 and annular opening 59 in the ceramic tip 55 are supplied with suction from the inner lumen 20 via lumen 60 of the mandrel 52. As illustrated in FIG. 15, cylindrical ceramic insulator 53 is assembled to the mandrel 52 and retained in position by the inner tube 25. The mandrel 52 is joined to the inner tube 25 by a weld 61. The cylindrical ceramic insulator 53 acts as a bearing to prevent binding during oscillation of the movable portion 51 within the fixed portion 50, particularly in the presence of lateral forces due to interaction between the electrosurgical ablator electrode and bone during ablation.

The polymeric insulating tubing 37 is a heat-shrink type tubing having a low coefficient of friction to allow ease of motion of the inner tube 25 within the outer tube 34. The polymeric insulating tubing 37 covers the inner tube 25 and the proximal-most portion 62 of the cylindrical ceramic insulator 53 to electrically insolate the inner tube 25 from the outer tube 34 in the presence of conductive fluids. As shown in FIGS. 13–15, a polymeric coating 72 covers end cap 58, the lower portions of lateral facing surfaces 70 and axial facing surfaces 71 of the ceramic top insulator 54, and exposed surfaces of the mandrel 52 except for electrodes 56. The polymeric coating 72 may be formed of a fused epoxy powder coat or a similar material.

Rotation of the electric motor 29 produces oscillations of the movable inner tube 25, the amplitude of the oscillations being determined by the design of the cam 31 affixed to the motor output shaft 30. FIGS. 9–11 illustrate the movable portion 51 at its distal-most position. FIG. 9 illustrates the movable portion 51 retracted to its proximal-most position. Thus, the amplitude of the oscillation 73 (FIG. 12) is the difference between the distal-most position and the proximal-most position of the movable portion 51. The amplitude of the oscillation 73 is of about 0.5 to about 5 millimeters, more preferably of about 1 to about 3 millimeters.

The electrosurgical ablator electrode 100 of the present invention described above with reference to FIGS. 1–15 may be employed in various electrosurgical procedures for which the "non-sparking" time of the electrosurgical ablator is minimized by employing mechanical debridement simultaneously with ablation. For example, the electrosurgical ablator electrode 100 (FIGS. 1–15) of the present invention may be employed in a variety of surgical medical procedures in the presence of an electrically conductive fluid to remove and/or modify a particular target tissue. Accordingly, the electrosurgical ablator electrode 100 of the of the present invention may be used in a conventional open surgery environment or in other, less invasive, techniques that use cannulas or various port access devices if conductive fluid is present. The present invention has also applications in surgical procedures where the target tissue is flooded with, or submerged in, an electrically conductive fluid such as in many arthroscopic procedures for ablation, coagulation, shaping and cutting of various body parts such as the knee, shoulder, hip, ankle, elbow, hand or foot.

The present invention has also equal applicability to surgical procedures where the target tissue is flooded with a natural conductive fluid of the human body, such as blood or lymphatic plasma, for example, which act as electrically conductive fluids. Nevertheless, an electrically conductive fluid introduced into the patient's body is preferred over blood because blood tends to coagulate at certain temperatures. In addition, the patient's blood or plasma may lack the necessary conductivity to adequately carry out the particular electrosurgical procedure desired.

Surgical procedures using the electrosurgical ablator electrode 100 of the invention include introducing the electrode in close proximity to the surgical site through an artificial conduit or a cannula, or through a natural conduit which may be in an anatomical body cavity or space or one created surgically. The cavity or space may be distended during the procedure using a fluid or may be naturally held open by anatomical structures. In addition, the surgical site may be bathed in a continiuous flow of conductive fluid, such as saline solution, to fill and distend the cavity. The procedures may include simultaneous viewing of the site via an endoscope or using an indirect visualization means.

Figure 16:
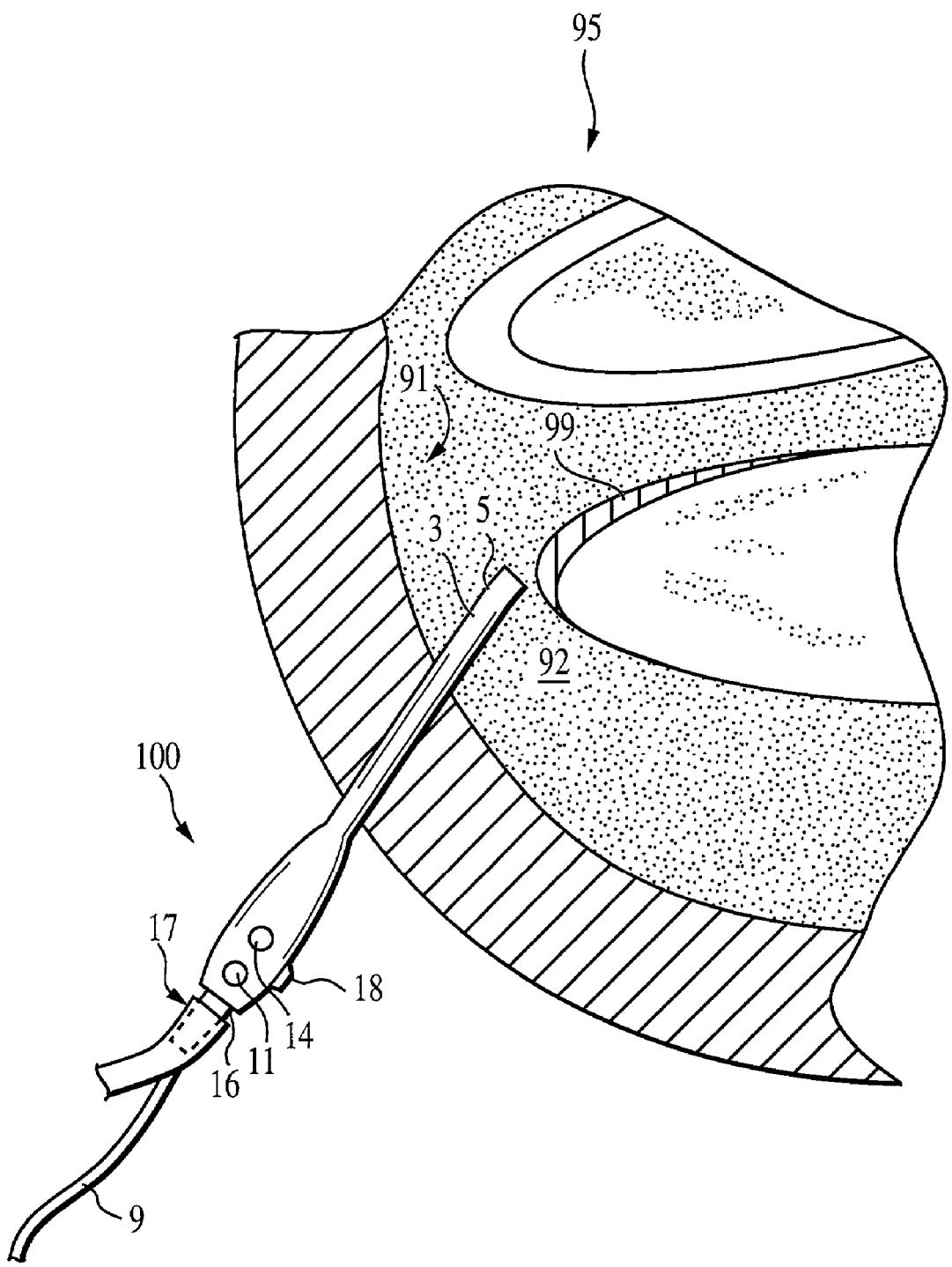
FIG. 16 is a schematic cross-sectional view of a knee joint undergoing an electrosurgical procedure employing an electrosurgical probe of the present invention.

To better illustrate an exemplary surgical procedure conducted with the electrosurgical ablator electrode 100 of the present invention, reference is now made to FIG. 16, which illustrates a schematic cross-sectional view of a knee joint region 95. The knee joint region 95 of FIG. 16 may undergo an arthroscopic procedure, for example, with electrosurgical ablator electrode 100 having the elongated distal active portion 3 provided with a combined oscillatory and mechanical debridement motion in accordance with the present invention.

As known in the art, an endoscope (not shown) may be introduced into knee cavity 92 (FIG. 16) containing electrically conductive fluid 91 (FIG. 16) and in close proximity to target tissue 99 (FIG. 16). If the target tissue 99 of the knee joint region 95 is a damaged meniscus, for example, then target tissue 99 may undergo a partial or complete electrosurgical meniscectomy using the electrosurgical ablator electrode 100. Knee cavity 92 is preferably distended during the arthroscopic procedure using electrically conductive fluid 91, so that target tissue 99 is bathed in a continuous flow of conductive fluid 91, preferably a saline solution.

Once the elongated distal active portion 3 of probe 100 is positioned in the proximity of the target tissue 99 and the target tissue 99 is submerged in the electrically conductive fluid 91, the surgeon moves the suction control slide 18 to the open position, thereby applying suction to the annular passages 58 and 59 (FIG. 15) which begin aspirating out fluid in the region of the electrode ablating surfaces. Subsequently, the surgeon depresses the first button 11 labeled "ABLATE" to activate the generator and initiate the oscillatory motion of the electrode tip 5 of the elongated distal active portion 3. This way, the electrosurgical ablator electrode 100 is energized by the electrosurgery power supply. The power supply delivers radio frequency energy, typically in the range of 100 kHz to 3 MHz, through the electrical cord 9 to the electrosurgical ablator electrode 100 and further to the elongated distal active portion 3.

The electrosurgical ablator electrode 100 is then removed and swept across the target tissue 99 with a brushing motion. Contact between the elongated distal active portion 3 and the target tissue 99 causes ablation to commence while the oscillatory, scraping motion of the electrode causes spent bubbles to be removed from the active electrode and some mechanical debridement to occur. Bubbles and debris formed by the process are aspirated from the knee joint region 95 by flow through the annular passages 58, 59 (FIG. 15) and the vacuum supplied to them.

Coagulation of bleeders is accomplished by depressing the second button 14 labeled "COAG." Oscillation of the electrosurgical ablator electrode 100 does not occur when the "COAG" button 14 is depressed.

In another variation, in the "COAG" mode and when the second button 14 is depressed, oscillation of the electrosurgical ablator electrode 100 occurs.

Once the tissue in a predetermined sparking region is mostly destroyed and further sparking does not destroy any additional tissue in this region, the elongated distal active portion 3 of the electrosurgical ablator electrode 100 may subsequently oscillate to another sparking region so that new tissue will be subjected to destruction.

Although the present invention has been described above with reference to arthroscopic surgery of a knee joint structure, the invention is not limited to such a procedure. Accordingly, the electrosurgical ablator electrode 100 (FIGS. 1-15) having an oscillatory motion coupled with a mechanical debridement motion may be employed for a variety of arthroscopic procedures, for example, in the dissection, resection, vaporization, desiccation and coagulation of tissue structures in various endoscopic and percutaneous procedures performed on joints of the body including, but not limited to, spinal and other non-synovial joint techniques.

Arthroscopic procedures encompassed by the present invention may further include: lateral retinacular release of the knee joint; removal of anterior and posterior cruciate ligaments; labral tear resection; acromioplasty, bursectomy and subacromial decompression of the shoulder joint; anterior release of the tempomandibular joint; synovectomy, cartilage debridement, chondroplasty, division of intra-articular adhesions, fracture and tendon debridement as applied to any of the synovial joints of the body; inducing thermal shrinkage of joint capsules as a treatment for recurrent dislocation, subluxation or repetitive stress injury to any articulated joint of the body; discectomy either in the treatment of disc prolapse or as part of a spinal fusion via a posterior or anterior approach to the cervical, thoracic and lumbar spine or any other fibrous joint for similar purposes; excision of diseased tissue and haemostasis, among others.

The oscillatory electrosurgical ablator electrode 100 (FIGS. 1–15) of the present invention may be also used in hysteroscopic surgical procedures or urological endoscopic (urethroscopy, cystoscopy, ureteroscopy and nephroscopy)

and percutaneous interventions. Hysteroscopic procedures may include: removal of submucosal fibroids, polyps and malignant neoplasms; resection of congenital uterine anomalies such as a septum or subseptum; division of synechiae (adhesiolysis); ablation of diseased or hypertrophic endometrial tissue; and haemostasis. Urological procedures may include: electro-vaporization of the prostate gland (EVAP) and other similar procedures commonly referred to as transurethral resection of the prostate (TURP) including, but not limited to, interstitial ablation of the prostate gland by a percutaneous or perurethral route whether performed for benign or malignant disease; transurethaal or percutaneous resection of urinary tract tumors; division of strictures as they may arise at the pelviureteric junction (PUJ), ureter, ureteral orifice, bladder neck or urethra; correction of ureterocoele, among others.

Although the above embodiments have been described with reference to an electric motor that is capable of imparting a linear oscillatory motion to the tip of the electrosurgical ablator electrode 100 of the present invention, the invention is not limited to the above-described embodiment. Accordingly, the present invention also contemplates an electrosurgical probe capable of imparting any oscillatory motion or other repetitive motion, for example, an axial oscillatory motion or an angular oscillatory motion, a rotatory motion such as a back-and-forth vibrational rotational motion, a vibratory motion, or any combination of such repetitive motions. Thus, the present invention contemplates an electrosurgical probe linked to various means of imparting a repetitive motion, for example, an oscillating circuit, a piezoelectric device or a rotating device, among others.

The present invention also contemplates mechanical means attached to the elongated distal active portion 3 of the electrosurgical ablator electrode 100 and powered by a gear mechanism driven by a motor, for example, which may be located within the handle 2. The gear mechanism may be further mounted within handle 2 and may be powered by a battery within the handle 2, or alternatively, by an external power supply. The gear mechanism may be also attached external to the handle 2 and to the elongated distal active portion 3, and may also be powered by either a battery or an external power supply.

The present invention also contemplates imparting a vibratory, rotatory or oscillatory motion to the elongated distal active portion 3 of the electrosurgical ablator electrode 100 by employing an eccentric weight affixed to the output shaft of an electric motor, which may be located within handle 2, for example. As in the previous embodiments, the electric motor may be powered and operated by a battery located within the handle 2 or by an external power supply. A vibrating magnetic mechanism, or an ultrasound mechanism or a pneumatic mechanism may be also employed to impart a vibratory or oscillatory motion to the elongated distal active portion 3 of the electrosurgical ablator electrode 100.

The above description and drawings illustrate preferred embodiments which achieve the objects, features and advantages of the present invention. It is not intended that the present invention be limited to the illustrated embodiments. Any modification of the present invention which comes within the spirit and scope of the following claims should be considered part of the present invention.

The invention claimed is:

1. A method of conducting an electrosurgical procedure comprising the steps of:
    positioning an active electrode of an electrosurgical probe in the proximity of a tissue to be treated in the presence of an electrically conductive fluid, said active electrode being substantially covered by an insulator and having a plurality of ribs individually protruding through and surrounded by said insulator, such that the electrode is exposed to said electrically conductive fluid only at an end portion of each of the ribs;
    applying a high frequency voltage to said active electrode and simultaneously imparting a repetitive motion having an amplitude of about 0.5 to about 5 millimeters to said active electrode to manage the formation of bubbles at said electrode to minimize unproductive non-sparking time by removing spent bubbles from said active electrode;
    manually activating a suction assembly for supplying adjustable suction from an external source, said suction being applied without automatic interruption through a passage in said probe, said passage terminating at the tip of said probe at a location spaced away from said active electrode; and
    effecting ablation of at least a portion of said tissue to be treated.

2. The method of claim 1, wherein said repetitive motion comprises an oscillatory motion.

3. The method of claim 1, further comprising the step of imparting a mechanical debridement motion to said active electrode.

4. The method of claim 1, wherein said suction is manually adjusted by manually controlling the opening or closing of said passage of said suction assembly, said passage allowing flow of debris from said tissue to be removed.

5. The method of claim 1 wherein said oscillatory motion is characterized by an amplitude of about 1 to about 3 millimeters.

6. The method of claim 1, wherein said step of activating said suction assembly aspirates debris from ablated tissue through said passage separate from said active electrode.

7. The method of claim 1, wherein said electrosurgical probe is a monopolar probe.

* * * * *